US009955695B2

(12) United States Patent
Found

(10) Patent No.: US 9,955,695 B2
(45) Date of Patent: *May 1, 2018

(54) PEDICULICIDE/OVICIDE COMPOSITION

(75) Inventor: John Found, West Perth (AU)

(73) Assignee: Wild Child, West Perth (AU)

( * ) Notice: Subject to any disclaimer, the term of this patent is extended or adjusted under 35 U.S.C. 154(b) by 662 days.

This patent is subject to a terminal disclaimer.

(21) Appl. No.: 12/093,985

(22) PCT Filed: Nov. 17, 2006

(86) PCT No.: PCT/AU2006/001720
§ 371 (c)(1),
(2), (4) Date: Oct. 6, 2008

(87) PCT Pub. No.: WO2007/056813
PCT Pub. Date: May 24, 2007

(65) Prior Publication Data
US 2009/0227687 A1    Sep. 10, 2009

(30) Foreign Application Priority Data
Nov. 18, 2005 (AU) ............................. 2005906399

(51) Int. Cl.
| | |
|---|---|
| *A61K 31/045* | (2006.01) |
| *A01N 49/00* | (2006.01) |
| *A01N 65/00* | (2009.01) |
| *A01N 65/08* | (2009.01) |
| *A01N 65/10* | (2009.01) |
| *A01N 65/12* | (2009.01) |
| *A01N 65/22* | (2009.01) |
| *A01N 65/24* | (2009.01) |
| *A01N 65/28* | (2009.01) |
| *A01N 65/36* | (2009.01) |
| *A01N 65/44* | (2009.01) |

(52) U.S. Cl.
CPC ............ *A01N 49/00* (2013.01); *A01N 65/00* (2013.01); *A01N 65/08* (2013.01); *A01N 65/10* (2013.01); *A01N 65/12* (2013.01); *A01N 65/22* (2013.01); *A01N 65/24* (2013.01); *A01N 65/28* (2013.01); *A01N 65/36* (2013.01); *A01N 65/44* (2013.01); *A61K 31/045* (2013.01)

(58) Field of Classification Search
CPC ........................... A01N 31/02; A61K 2300/00
USPC ........................................................ 514/739
See application file for complete search history.

(56) References Cited

U.S. PATENT DOCUMENTS

| | | | | |
|---|---|---|---|---|
| 4,933,371 A | * | 6/1990 | Hink et al. .................... | 514/739 |
| 6,258,369 B1 | | 7/2001 | Pullen | |
| 6,342,253 B1 | | 1/2002 | Whitledge | |
| 6,607,716 B1 | | 8/2003 | Smith et al. | |
| 6,656,928 B1 | * | 12/2003 | McCadden ................... | 514/167 |
| 6,727,228 B2 | * | 4/2004 | Janssen et al. ................ | 514/28 |
| 6,911,196 B2 | * | 6/2005 | Hamtini ..................... | 424/78.08 |
| 6,914,077 B2 | * | 7/2005 | Nagatsuka et al. ........... | 514/557 |
| 2002/0187168 A1 | | 12/2002 | Jensen et al. | |
| 2005/0019431 A1 | * | 1/2005 | Modak et al. ................ | 424/736 |
| 2005/0186161 A1 | * | 8/2005 | Kawase et al. ................ | 424/61 |
| 2006/0008486 A1 | * | 1/2006 | Lewis .......................... | 424/401 |

FOREIGN PATENT DOCUMENTS

| | | |
|---|---|---|
| CH | 688 787 A | 3/1998 |
| EP | 1 048 293 A | 11/2000 |
| GB | 1 593 601 | 7/1981 |
| GB | 2 341 091 A | 3/2000 |
| JP | 07-118145 * | 5/1995 |
| JP | 2000-026210 | 1/2000 |
| WO | WO 00/64265 | 11/2000 |
| WO | WO 01/26471 A | 4/2001 |
| WO | WO 02/076423 A2 | 10/2002 |
| WO | WO 02/076423 A3 | 10/2002 |

OTHER PUBLICATIONS

English translation of JP 07-118145 (1995).*
G. Della Porta et al., Isolation of Clove Bud and Star Aniese Essential Oil by Supercritical $Co_2$ Extraction, LWT-Food Science and Technology, Aug. 1, 1998, pp. 454-460, vol. 31, No. 5, Academic Press, Italy.
Narayanan Gopalakrishnan et al., Composition of Clove (*Syzygium aromaticum*) Bud Oil Extracted Using Carbon Dioxide, Journal of the Science of Food and Agriculture, Jan. 31, 1990, pp. 111-117, vol. 50, Society of Chemical Industry, India.
S. M Njoroge et al., Volatile Components of Japanese Yuzu and Lemon Oils, Flavour and Fragrance Journal, Aug. 31, 1994, pp. 159-166, vol. 9, John Wiley & Sons Ltd, Japan.
Examination Report from EuropeanPatent Office for corresponding application EP 06804533.5 dated May 15, 2015.
Tarabet et al. Eucalyptus Biodiesel as an Alternative to Diesel Fuel: Preparation and Tests on DI Diesel Engine, J. of Biomedicine and Biotechnology, 8 pgs., vol. 2012, Article ID 235485.
Thamilselvan, et al., Experimental Analysis of Direct Injection Diesel Engine Using Palmarosa Oil, J. of Mechanical and Civil Engineering, pp. 8-17, ISSN: 2278-1684.
Metin et al., Use of Hazelnut Kernel Oil Methyl Ester and Its Blends as Alternative Fuels in Diesel Engines, Turkish J. Eng. Env. Sci, (2008) pp. 133-141.
Siddiqui, N. et al., A Study on Viscosity, Surface Tension and Volume Flow Rate of Some Edible and Medicinal Oils, Int'l J. of Science Environment and Technology, 1318-1326, vol. 2, No. 6, 2013.
Weiman, Safety Data Sheet, Lemon Oil, Nov. 13, 2014.
Table Concerning Harmonious Blends (noting viscosity).

* cited by examiner

*Primary Examiner* — Bong-Sook Baek
(74) *Attorney, Agent, or Firm* — McCarter & English, LLP

(57) ABSTRACT

The present invention relates to a pediculicide/ovicide composition and method of use thereof. In particular, the present invention relates to a pediculicide/ovicide composition comprising a sesquiterpene alcohol and a suitable carrier.

4 Claims, 2 Drawing Sheets

PEDICULICIDE/OVICIDE COMPOSITION

This application is a 371 of PCT/AU2006/001720 filed on Nov. 17, 2006, published on May 24, 2007 under publication number WO 2007/056813 A and claims priority benefits of Australian Patent Application No. 2005906399 filed Nov. 18, 2005, the disclosure of which is hereby incorporated by reference.

FIELD

The present invention relates to a pediculicide/ovicide composition and method of use thereof. In particular, the present invention relates to a pediculicide/ovicide composition comprising a sesquiterpene alcohol derived from essential oil.

BACKGROUND

Lice belong to the order Phthiraptera, and are the only truly parasitic group amongst the exopterygote insects. As permanent ectoparasites of most birds and mammals they exhibit a remarkable level of host specificity which is unparalleled in most other metazoan parasites. To date there are more than 3000 known species of lice and yet many more remain undescribed. With the possible exception of those species that impinge on the activity of humans and their livestock, the true biology of this cryptic group of insects remains obscure. The order Phthiraptera has been traditionally divided into two groups according to their different feeding habits: the chewing lice or "*Mallophaga*", and the Anoplura, colloquially known as the "sucking lice".

Chewing lice with their large head and mandibles comprise the largest group with some 2900 species, while the Anoplura comprise some 500 species. The Anoplura are restricted to mammals and feed using maxillae positioned at the end of a snout-like protrusion to pierce the skin. Feeding solely on blood they remain at the feeding site causing localized skin irritations to their host. Because of this they are the vectors to a number of blood borne diseases. This group includes the human louse *Pediculus humanus*, consequently they are probably the most well studied louse group.

Because of their potential to spread disease lice have been studied extensively with respect to control. Lice infestation has traditionally been treated using pesticides or pediculicides comprising nervous system toxicants capable of inhibiting or over-potentiating synapse-synapse and/or neuromuscular junction transmission, many acting specifically as acetylcholinesterase inhibitors.

Representative examples of pesticides include: 1) chlorinated phenyl and cyclodiene compounds such as DDT, chlordane, heptachlor, and aldrin and dieldrin; 2) the carbamate esters carbaryl, carbofuran, aldicarb, and baygon; 3) organic thiophosphate esters such as diazinon, Malathion, parathion, and dicapthon; and 4) the synthetic pyrethroids allethrin, permethrin, resmethrin, and fenvalerate.

While these and other pediculicides have been used extensively and to good effect, they present risks to human and animal health. For example, many of the regularly used pediculicides present some direct risk to human health through residual toxicity, i.e. through direct human contact with pesticide residues. Other pesticides produce volatile toxic vapours, which can cause skin irritation on absorption or ingestion. In addition, many pediculicides present indirect risks to human health in the form of environmental pollution, most notably pollution with persistent, halide-substituted organics, which accumulate in the fat stores of food fish and other animals. These problems have led to complete bans on the use of some agents eg, DDT, chlordane, heptachlor, aldrin, and dieldrin.

There is also increasing concern that many of the known pediculicides are becoming less effective than previously experienced. For example, many of the known pediculicides have been noted to be ineffective in killing the ova or nits of lice. Thus, the use of these pediculicides results in a reinfestation of the hair or skin as soon as the ova hatch, since the treatment was ineffective in controlling and killing the ova. Accordingly, the combination of health and environmental concerns coupled with the less effectiveness of known pediculicides has resulted in a need to develop an effective treatment for both adult lice and their ova.

SUMMARY

The inventor has surprising found that a composition comprising an effective amount of sesquiterpene alcohol-containing essential oil is effective as a pediculicide and ovicide.

Accordingly, in a first aspect the present invention provides a pediculicide/ovicide composition comprising sesquiterpene alcohol and a suitable carrier.

In some embodiments, the sesquiterpene alcohol is derived or isolated from an essential oil selected from the group consisting of lemon oil, verbena oil, geranium oil, anise oil, patchouli oil, lavender oil, boronia oil, eucalyptus oil, tea tree oil, bay oil, sandalwood oil, orange oil, citronella oil, grapefruit oil, jasmine oil, cinnamon oil, chamomile oil, clary sage oil, lime oil, mandarin oil, palma *rosa* oil, rosewood oil, ylang ylang oil, hazelnut oil and nutmeg oil.

In some embodiments, the sesquiterpene alcohol is present as essential oils per se such sandalwood oil extracted from sesquiterpene alcohol-containing sandalwood.

The compositions of the present invention may further comprise other essential oils such as sandalwood oil, geranium oil, lavender oil and eucalyptus oil. These essential oils may assist the pediculicide and/or ovicide activity of the composition by, for example, helping the composition to penetrate the lice egg walls ("ova").

The composition may also be mixed with conventional pediculicide acceptable excipients, stabilizers, diluents or extenders usable in the art. If desired, adjuvants such as surfactants, stabilizers and antifoam agents may also be added.

In some embodiments, the pediculicide/ovicide compositions of the present invention further comprise from about 1% to about 10% of a stabilizer selected from the group consisting of glyceryl monostearate, stearic acid, triethanolamne, ethanol, polysorbate 20, cetyl alcohol, stearyl alcohol, cetrimonium bromide, citric acid, cyclomethicone, dimethicone, ceteth 20, ceteareth 20, caprylic/capric triglycerides, PEG 40 polyhydroxystearate, polyvinyl pyrrolidone, acetum, glyceryl stearate, xanthan gum, geranium oil, lavender oil, eucalyptus oil, tea tree oil, lemon oil, anise oil, DEA cetyl phosphate, sodium stearate, potassium stearate, wool alcohols, octyl stearate, carnauba wax, ozokerite, carbomer, phenoxyethanol, methyl parabens and propyl parabens and mixtures thereof.

The formulation of the compositions will depend upon the end use and methods of developing such formulations are well within the skill of persons in the art. Formulations include creams, shampoos, ointments, aqueous suspensions and dispersions, oily dispersions, pastes, dusting powders, wettable powders flowables, granules, aerosols and emulsions.

In some embodiments of the present invention the essential oils are extracted from plants known to contain essential oils which oil comprises sesquiterpene alcohol. In some embodiments, the essential oil containing plants include *Cyperus*, lemon, geranium, lavender, boronia, eucalyptus, tea tree, sandalwood, orange, jasmine, cinnamon, chamomile, rose, hazelnut and nutmeg.

In some embodiments, the essential oil containing plants are one or more of *Cyperus iria, Cyperus microiria* Steud, *Cyperus monophyllus* Vahl., *Cyperuspilosus* Vahl., *Cyperus serotinus* Rottb and *Santalum spicatum*.

In some embodiments the sesquiterpene alcohol is a compound of general formula I:

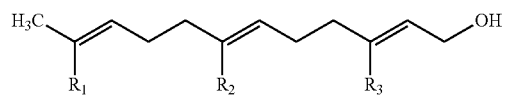

wherein $R_1$, $R_2$ and $R_3$ are independently $CH_3$, H or OH.

In some embodiments the sesquiterpene alcohol is either farnesol or nerolidol and their derivatives.

In some embodiments, the concentration of farnesol or nerolidol used is less than about 3% w/w.

In second aspect, the present invention provides a method for removing lice of the order Phthiraptera from hair or skin and/or killing said lice comprising the step of applying a pediculicide/ovicide composition comprising sesquiterpene alcohol and a suitable carrier to the hair or skin for sufficient time to facilitate the subsequent removal or death of the fleas or lice.

The pediculicide/ovicide composition may be applied either directly to lice or applied to a locus comprising the lice including an area-wide application of the pediculicide composition.

It will be appreciated by those skilled in the art that the pediculicide/ovicide composition can be applied to any animal or object which is likely to come into contact with lice. Non-limiting representative species of lice include head lice, body lice and crab lice as well as the eggs (ova or "nits") associated with these organisms.

In a third aspect the present invention provides a method for controlling lice of the suborder Anoplura comprising the step of topically applying to one or more of skin and hair a lice treatment agent having pediculicidal/ovacidal properties said agent comprising sesquiterpene alcohol and a suitable carrier, wherein said agent is applied to the hair or skin for sufficient time to facilitate the control of the lice.

In a fourth aspect the present invention provides a method for controlling lice of the suborder *Mallophaga* comprising the step of topically applying to one or more of skin and hair a lice treatment agent having pediculicidal/ovacidal properties said agent comprising sesquiterpene alcohol and a suitable carrier, wherein said agent is applied to the hair or skin for sufficient time to facilitate the control of the lice.

In some embodiments, the methods of the second, third and fourth aspects further comprise the steps of:
(b) removing the composition from the hair after a substantial portion of the lice are killed;
(c) removing the dislodged lice from the hair or skin.

In a fifth aspect the present invention provides a method of treating human hair to kill and facilitate removal of lice of the order Phthiraptera and their eggs comprising:

(a) applying from about 10 g to about 30 g of a pediculicide comprising sesquiterpene alcohol and a suitable carrier to hair;
(b) working said composition through the hair and scalp;
(c) leaving the composition on the hair and scalp for about 10 minutes to about 24 hours; and
(d) rinsing said composition from the hair.

In a sixth aspect the present invention provides a kit for the removal, treatment or prevention of lice infestation comprising
a) an amount of a pediculicide composition comprising sesquiterpene alcohol and a suitable carrier; and
b) instructions effective to perform the removal of lice or fleas.

DETAILED DESCRIPTION OF THE PREFERRED EMBODIMENTS

Figure 1:
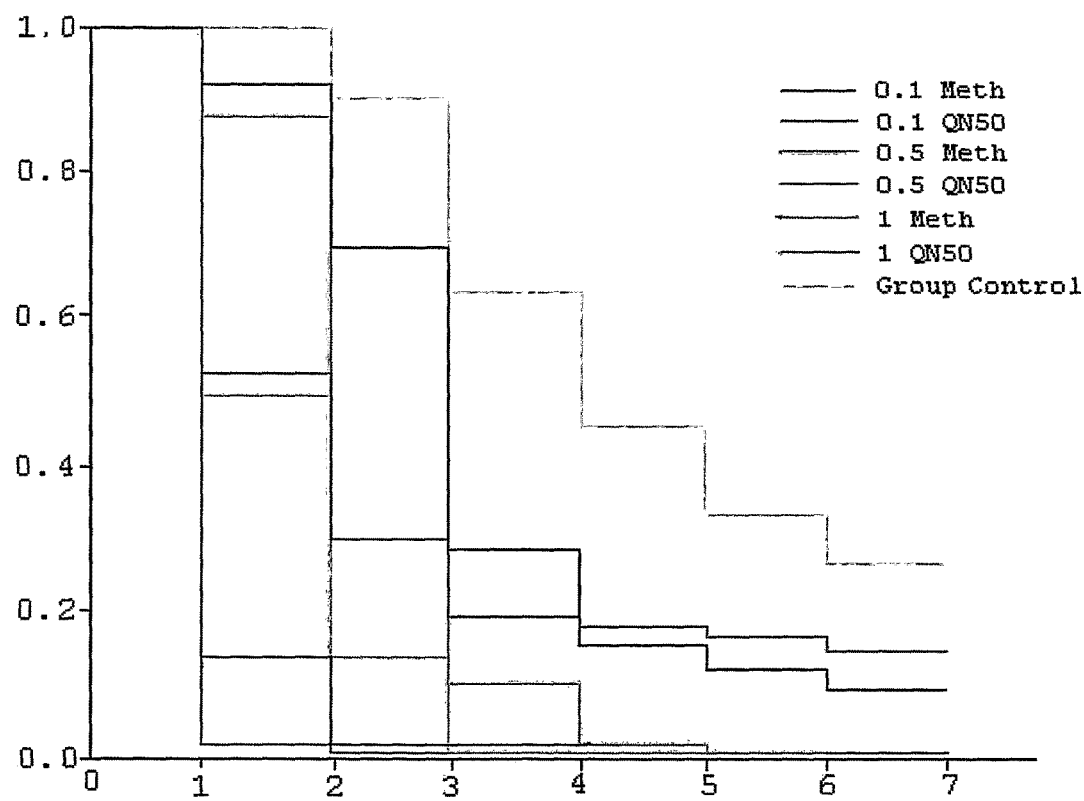
FIG. 1 shows the survival probability of mosquito larvae exposed to different concentrations of QN50 or methoprene.
Figure 2:
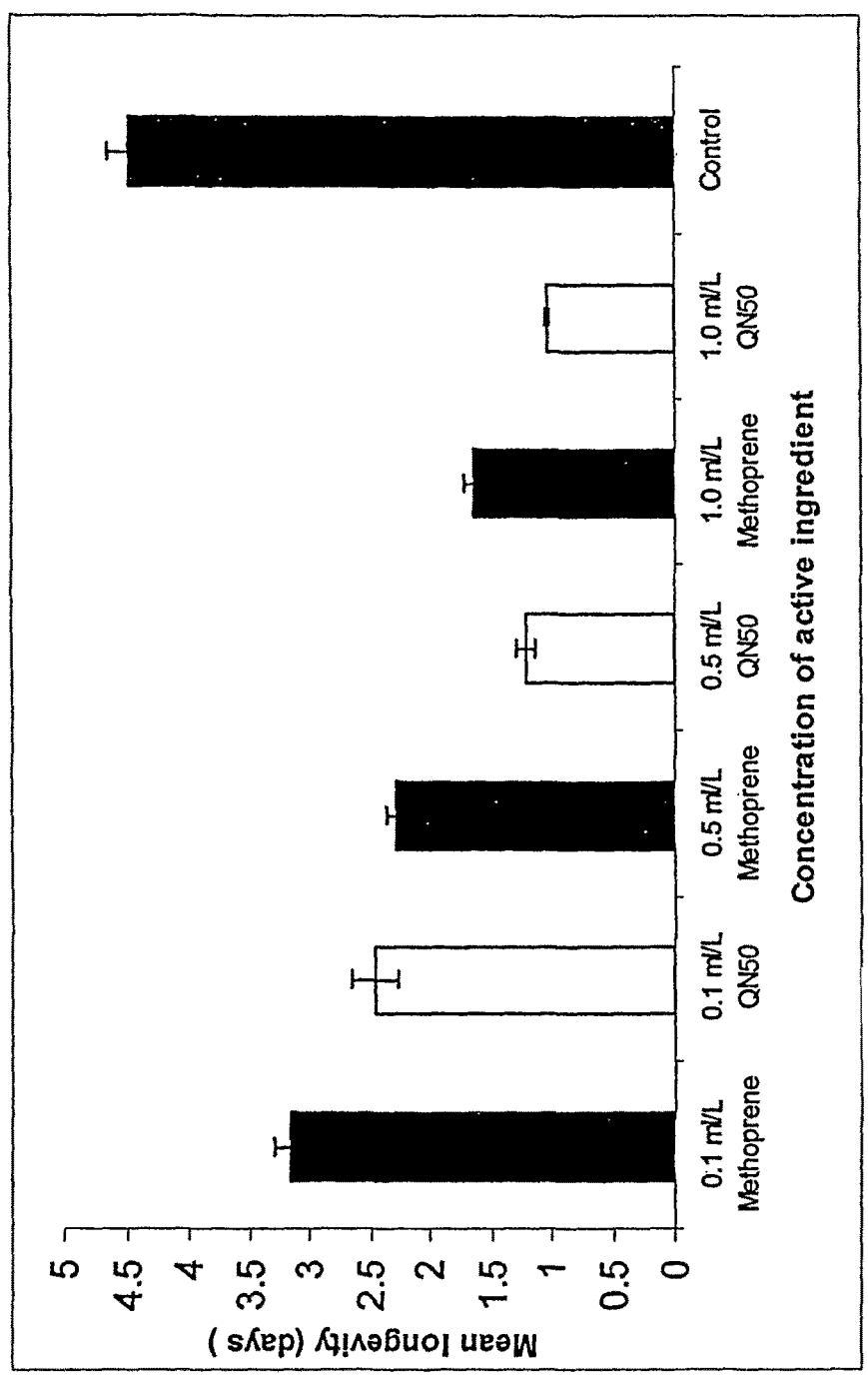
FIG. 2 shows average longevity (+S.E.M.) of mosquito larvae exposed to different concentrations of either methoprene (black bars), QN50 (white bars), or a control (source water only) over seven days.

All publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention employs, unless otherwise indicated, conventional chemistry within the skill of the art. Such techniques are well known to the skilled worker, and are explained fully in the literature. See, eg., Vogel and Furniss, 1989, "Vogel's textbook of practical organic chemistry", Longman Publishers; 1979; and Huheey, J., 1983, "Inorganic Chemistry $3^{rd}$ Edition", Harper International.

The description that follows makes use of a number of terms used in chemistry. Unless defined otherwise, all technical and scientific terms used herein have the meaning commonly understood by a person skilled in the art to which this invention belongs. The following references provide one of skill with a general definition of many of the terms used in this invention: "The Cambridge Dictionary of Science and Technology" (Walker ed., 1988); Hale & Marham, "The Harper Collins Dictionary of Biology" (1991); "Nomenclature of organic chemistry" $4^{th}$ Edition Pergamon Publishers (1979); "Henderson's dictionary of biological terms" (Lawrence, Eleanor (ed.)) $12^{th}$ Edition, Prentice Hall Publishers (2000); and "Oxford Dictionary of Chemistry", $4^{th}$ Edition, (Daintith, John (ed)) 2000, Oxford University Press.

Generally, the nomenclature and the laboratory procedures used in chemistry as described herein are those well known and commonly employed in the art.

It is understood that the invention is not limited to the particular materials and methods described, as these may vary. It is also to be understood that the terminology used herein is for the purpose of describing particular embodiments only, and it is not intended to limit the scope of the present invention which will be limited only by the appended claims. It must be noted that as used herein and in the appended claims, the singular forms "a", "an", and "the" include plural reference unless the context clearly dictates otherwise. Thus, for example, a reference to "a sesquiterpene alcohol" includes a plurality of such sesquiterpene alcohols, and a reference to "an animal" is a reference to one or more animals, Although any materials and methods similar or equivalent to those described herein can be used to practice or test the present invention, the preferred materials and methods are now described.

In its broadest aspect the present invention is directed towards a pediculicide/ovicide composition comprising sesquiterpene alcohol and a suitable carrier.

The term "pediculicide" as used herein refers to a composition of the present invention comprising or consisting of at least one sesquiterpene alcohol, which is capable of decreasing the number of live lice of the order Phthiraptera and viable ova ("nits") (referred to as ovicide) found on the hair or skin of a host or its environment.

"Lice" means any of various small, flat-bodied, wingless, biting or sucking insects of the order Phthiraptera present as an external parasite on hair-bearing surfaces of various animals. Thus, the term lice encompass all species within the suborders Anoplura and *Mallophaga* including the following families: echniophtiriidae, enderleinellidae, haematopimidae, linognathidae, pecaroecidae, pediculidae, polyplacidae, and pthiridae. Examples of species in the suborder Anoplura include, but are not limited to pediculus humanus, pediculus capitis, and pthiris pubis. These three species are known more commonly as the body louse, head louse, and pubic louse.

The louse may be either the adult louse or the lice egg (e.g., nit). The human lice genera include pubic lice (Pthirus pubis, or Phthirus pubis), body lice (Pediculus Humanus var. *corporis*), and head lice (Pediculus humanus var. *capitis*).

The term "skin" as used herein refers to the epidermis of an animal, preferably a mammal, most preferably a human. Skin that would be commonly prone to lice includes that of the scalp, body, and pubis areas.

The term "sesquiterpene alcohol", according to the teaching of the present invention, can be any sesquiterpene alcohol ($C_{15}$ terpene alcohol) found in essential oils such as lemon oil, verbena oil, geranium oil, anise oil, patchouli oil, lavender oil, boronia oil, eucalyptus oil, tea tree oil, bay oil, sandalwood oil, orange oil, citronella oil, grapefruit oil, jasmine oil, cinnamon oil, chamomile oil, clary sage oil, lime oil, mandarin oil, palma *rosa* oil, rosewood oil, ylang ylang oil, hazelnut oil and nutmeg oil, which is capable of pediculicide/ovicide activity. For example, a suitable sesquiterpene alcohol can be farnesol, hinesol, agarospirol, valerianol, β-bisabolol, α-bisabolol, γ-eudesmol, ar-turmerol, α-copaen-11-ol, [E]-nerolidol; grossonorol, or taucadinol.

Preferably, the present invention utilizes a plurality of sesquiterpene alcohols acting in synergy in controlling lice or their ova.

As is illustrated in the Examples section which follows, sesquiterpene alcohols can be isolated as enriched fractions from a number of plants including *Cyperus*, lemon, geranium, lavender, boronia, eucalyptus, tea tree, sandalwood oil, orange, jasmine, cinnamon, chamomile, rose, hazelnut, nutmeg, ginger, patchouli, vetiver, carrot seed, everlasting and valerian. Crude essential oils from these plants can be prepared by cutting fresh cuttings into slices or pieces, followed by drying and grinding the dry tissue into a powder. The powder is then extracted by way of steam distillation or organic solvent extraction. Solvents like ethanol and acetone are suitable solvents for extraction of essential oils. Steam distillation is considered to be the best way to produce the crude oil. Principally, essential oil can be produced by liquid extraction, using a non-polar solvent like light petroleum ether or hexane. Once obtained, the crude essential oil is fractionated by chromatography methods so as to isolate the fractions containing sesquiterpene alcohols. A number of chromatography and separation methods can be used, including high-pressure liquid chromatography (HPLC), column chromatography, and distillation under low pressure, all of which are well known in the art. Alternatively, sesquiterpene alcohols, or analogs, or derivatives thereof may be chemically synthesized using methods known in the art, such as described, for example, by Meyers & Smith (*Tetrachedron Letters,* 1979, 2749) or by Sato et al. (*Tetrachedron Letters,* 1980, 3377).

The composition can comprise a single sesquiterpene alcohol, more than one sesquiterpene alcohol, a liposome-sesquiterpene alcohol combination, or combinations thereof. Mixtures of sesquiterpene alcohols can produce synergistic effects.

All classifications of natural or synthetic sesquiterpene alcohol will work in this invention. However, the method of acquiring the sesquiterpene alcohol is not critical to the operation of the invention.

The concentration of sesquiterpene alcohol or combination thereof in the pediculicide is described as an "effective amount". The term "effective amount" means an amount of sesquiterpene alcohol sufficient to decrease the number of live lice and viable ova. The effective amount can typically range from about 2 ppm to about 3% (15000-30000 ppm). This amount can vary depending on the sesquiterpene alcohol used, the form of sesquiterpene alcohol (e.g., cream, lotion and the like), the lice species targeted, and other parameters that would be apparent to one of skill in the art. One of skill in the art would readily be able to determine the effective amount for a given application based on the general knowledge in the art and guidance provided in the procedures in the Examples given below. In one example, the sesquiterpene alcohol is farnesol and the amount is 5,000 ppm.

Concentrations of sesquiterpene alcohol of about, for example, 2, 20, 30, 40, 50, 60, 70, 80, 90, 100, 110, 125, 130, 140, 150, 175, 200, 225, 250, 300, 350, 400, 450, 500, 600, 750, 800, 1000, 1100, 1250, 1425, 1500, 1750, 2000, 2250, 2500, 3000, 3500, 4000, 4250, 4500, or 4750 ppm can be used as effective amounts in the compositions and methods of the current invention.

Concentrations of any other ingredients or components can also be readily determined by one of skill in the art using methods known in the art and demonstrated below.

However, when the term "effective amount" is used in reference to solvents, solubilizing agents or solutions, the term means that the solvents solubilize the pediculicide and/or ovacide composition and also that the solution has a concentration that effectively controls the lice and ova.

In some embodiments of the present invention the sesquiterpene alcohol is an extract from sandalwood oil. One type of sandalwood oil that is preferred is derived from *Santalum spicatum.*

In some embodiments the sesquiterpene alcohol pediculicide is a compound of general formula I:

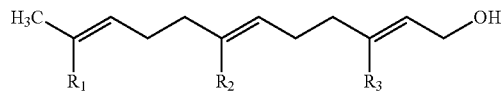

wherein $R_1$, $R_2$ and $R_3$ are independently $CH_3$, H or OH.

In some embodiments the sesquiterpene alcohol pest control agent is farnesol, nerolidol and their derivatives.

In some embodiments, the present invention provides a pediculicide/ovicide composition consisting of either farnesol or nerolidol or their derivatives and a suitable carrier. In some embodiments, the pediculicide/ovicide composition consists of or consists essentially of farnesol and a suitable carrier.

The composition can further comprise additional ingredients. For example, water or any animal-compatible diluent or carrier, surfactants (cleansing, emulsifying and/or foam-boosting surfactants), humectants, buffering agents, chelating agents, preservatives, pH Adjusters, moisturizers, antioxidants, conditioning agents, adjuvants, stabilizers and vehicles.

In some embodiments, the pediculicide composition of the present invention is formulated for topical use by combining the sesquiterpene alcohols with one or more surfactants. Examples of surfactant include polysorbate 20, polysorbate 80, polysorbate 40, polysorbate 60, polyglyceryl ester, polyglyceryl monooleate, decaglyceryl monocaprylate, propylene glycol dicaprilate, triglycerol monostearate, TWEEN, SPAN 20, SPAN 40, SPAN 60, SPAN 80, or mixtures thereof.

The term "cleansing surfactant" as used herein refers to one or more compounds used for skin and/or hair cleaning, and the cleansing surfactants are used in an amount which produces the desired function provided that the amount does not affect the stability of the sesquiterpene alcohols. These compounds can also serve as cosmetic emulsifiers. Classes of compounds include soaps and fatty acids/alkali combinations. Examples include, but are not limited to, ammonium lauryl sulphate, ammonium laureth sulphate, sodium lauryl sulphate, sodium laureth sulphate. For a more complete listing of cleansing surfactants, herein incorporated by reference, see Wenniger and McEwen, eds., 2 International Cosmetic Ingredient Dictionary and Handbook 1789-1795 (2000 ed.) (hereinafter termed "CFTA Dictionary").

In other embodiments, "emulsifying surfactants" are incorporated into the pediculicide composition. Emulsifying surfactants include compounds that reduce the surface tension and the emulsifying surfactants are used in an amount which produces the desired function provided that the amount does not affect the stability of the sesquiterpene alcohols. They create barriers around droplets to prevent them from coalescing. Emulsifiers could be, but are not limited to oil-in-water emulsifiers, water-in-oil emulsifiers, water-in-oil-in-water emulsifiers, oil-in-water-in-oil emulsifiers, silicone-in-water emulsifiers, and water-in-silicone emulsifiers. Examples include, but are not limited to, glyceryl trioleate, acetylated sucrose distearate, sorbitan trioleate, polyoxyethylene (1) monostearate, glycerol monooleate, sucrose distearate, polyethylene glycol (50) monostearate, octyl phenoxypoly(ethyleneoxy) ethanol, deacylerin penta-isostearate, sorbitan sesquioleate, hydroxylated lanolin, lanolin, triglyceryl diisostearate, polyoxyethylene (2) oleyl ether, calcium stearoyl-2-lactylate, cetearyl glucoside, methyl glucoside sesquistearate, sorbitan monopalmitate, methoxy polyethylene glycol-22/dodecyl glycol copolymer, polyethylene glycol-45/dodecyl glycol copolymer, polyethylene glycol 400 distearate and glyceryl stearate, cetyl phosphate, potassium cetyl phosphate. See also CFTA Dictionary 1796-1803.

In other embodiments, the pediculicide compositions of the present invention are combined with "foam-boosting surfactants", which are compounds that have the ability to either generate or stabilize foams and the foam-boosting surfactants are used in an amount which produces the desired function provided that the amount does not affect the stability of the sesquiterpene alcohols. They generally increase the surface viscosity of the vehicle surrounding the bubbles. Examples of foam-boosting surfactants include, but are not limited to, cocamidoethyl betaine, cetyl betaine, disodium cetearyl sulfosuccinate, disodium oleoamphodipropionate, lauramide DEA, lauramidopropyl betaine. See also CFTA Dictionary, 1803-1804.

As the pediculicide compositions of the present invention are generally used to treat hair and skin of an animal, it may be desirable to include "conditioning agents" in the formulations. Both skin and hair conditioning agents can be used. Skin conditioning agents include compounds that soften and smooth the skin and in an amount which produces the desired function provided that the amount does not affect the stability of the sesquiterpene alcohols. These compounds achieve this effect by lubricating the skin surface, encouraging skin water retention, and altering product textures. Examples include, but are not limited to, octyl hydroxystearate, lanolin, capric/caprylic triglyceride, cetyl palmitate, cetyl alcohol, isopropyl isostearate, glyceryl dilaurate, isopropyl myristate, palm alcohol, and sucrose cocoate. See also CTFA Dictionary 1768-1773.

"Hair conditioning agents" are compounds that can alter the texture, appearance, styling, or feel of the hair. Examples include, but are not limited to, alanine, arginine, biotin, calcium panthothenate, dimethicone, cyclomethicone, hydrolyzed plant protein, and polyquaterniums, preferably stearalkonium chloride, sold under the name Ammonyx-4 by Stepan Company. See CFTA Dictionary 1752-1759.

In some embodiments, humectants are also incorporated into the pediculicide compositions of the present invention. What is meant by "humectants" is one or more compounds that prevent the skin from losing moisture and the humectants are used in an amount which produces the desired function provided that the amount does not affect the stability of the sesquiterpene alcohols. Examples include, but are not limited to, glycerin, glucose, honey, lactic acid, polyethylene glycol, propylene glycol, sorbitol, sucrose, and trehalose. See also CFTA Dictionary 1773-1774.

If buffering agents are required then compounds that can maintain a desired pH in an aqueous environment are used. Examples include, but are not limited to, boric acid, citric acid, lactic acid, fumaric acid, phosphoric acid, and salts thereof. See also CFTA Dictionary 1733-1734.

In some embodiments, it may be desirable to use "chelating agents", which are compounds that can complex and subsequently inactivate ions in the pediculicide compositions and the chelating agents are used in an amount which produces the desired function provided that the amount does not affect the stability of the sesquiterpene alcohols. Examples include citric acid, disodium edetate, pentapotassium triphosphate, and phytic acid. See also CFTA Dictionary 1734-1735.

Once the required pediculicide compositions are prepared then in some embodiments "preservatives" are included to prevent or reduce or slow down microbial growth. The amount of preservative used will depend upon the preservative used and is well within the skill of the art to determine. Examples include, but are not limited to, benzoic acid, butylparaben, ethylparaben, propylparaben, methylparaben, sorbic acid, phenoxyethanol, and triclosan. See CFTA Dictionary 1765-1766.

pH Adjusters are also present in some embodiments of the invention and the pH Adjusters are used in an amount which produces the desired function provided that the amount does not effect the stability of the sesquiterpene alcohols. "pH adjuster" are acids or bases that can be used to adjust the pH of the finished pediculicide composition to the desired level. Examples include, but are not limited to, acetic acid, ammonia, citric acid, ethanolamine, formic acid, oxalic acid, potassium hydroxide, sodium hydroxide, and triethanolamine. See CFTA Dictionary 1764.

Further embodiments of the pediculicide compositions of the present invention may include one or more moisturizers, preferably propylene glycol and the moisturizers are used in an amount which produces the desired function provided that the amount does not affect the stability of the sesquiterpene alcohols. Additionally, emulsifying agents may be desirable, preferably Ceteareth-20, manufactured by Promateen Chemicals Inc., which is a polyethylene glycol ether of cetearyl alcohol. Ceteareth-20 has 20 moles of ethylene oxide which is added to the non-ionic surfactant to increase its water solubility. In the event that an emulsion stabilizer is used, the preferred one is a mixture of cetyl and stearyl alcohols, sold by Croda Inc. under the name Cetearyl alcohol.

In order to prevent the degradation caused by oxidation, antioxidants may be included in the pediculicide compositions and the antioxidants are used in an amount which produces the desired function provided that the amount does not affect the stability of the sesquiterpene alcohols. Antioxidants include, but are not limited to free radical scavengers and reducing agents such as, acetyl cysteine, ascorbic acid, butylated hydroxytoluene, green tea extract, caffeic acid, cysteine, tocopherol, ubiquinone, and propyl gallate, preferably butylated hydroxytoluene ("BHT"). See CFTA Dictionary 1727.

In other embodiments, in addition to the sesquiterpene alcohols, pH Adjusters, chelating agents, humectants and the like, the pediculicide compositions can further comprise adjuvants and the adjuvants are used in an amount which produces the desired function provided that the amount does not effect the stability of the sesquiterpene alcohols. Examples of adjuvants include, but are not limited to vehicles, stabilizers, moisturizers, cleansing surfactants, emulsifying surfactants, emulsifying stabilizers, foam-boosting surfactants, emollient skin conditioning agents, humectants, hair conditioning agents, buffering agents, pH adjusters, chelating agents, antioxidants, preservatives, botanical extracts, fragrances, and dyes.

In another embodiment, the pediculicide composition includes one or more stabilizers to prevent physical separation of the formulation ("stabilizers"). Non-acrylic decadiene cross polymers, including but not limited to Stabileze QM and Stabileze 06 (preferably Stabileze QM) manufactured by International Specialty Products may be employed to stabilize and optionally to thicken the formulations. Stabileze QM and Stabileze 06 are benzene-free copolymers of methyl vinyl ether/maleic anhydride crosslinked with 1,9-decadiene. The INCI name for Stabileze 06 and Stabileze QM is PVM/MA Decadiene crosspolymers. Stabileze 06 has a particle size of <850.mu.. Stabileze QM has a particle size of <75 µm Since Stabileze QM has a smaller particle size; it may be dispersed faster than Stabileze 06 and may be more rapidly converted to a gel. In some embodiments, a neutralizer of the stabilizer may be required to neutralize the formulation to an approximate pH of 5.5 in order to allow thickening of the formulation. A preferred neutralizer is sodium hydroxide.

Stabilizers may also include, but are not limited to, acrylates/aminoacrylates $C_{10\text{-}30}$ Alkyl PEG-20 Itaconate copolymer, long chain acyl derivatives (including, but not limited, to ethylene glycol distearate and ethylene glycol monostearate), alkanoamides (including but not limited to cocamide MEA), esters of long chain fatty acids (including but not limited to stearyl stearate), alkyl dimethylamine oxides, methylcellulose, hydroxybutyl methylcellulose, hydroxypropylcellulose, hydroxypropyl methylcellulose, hydroxyethyl cellulose, distearyl phthalic amide (e.g. Stephan SAB-2), di(hydrogenated) tallow phthalic amide (e.g. Stephan TAB-2), primary amines with a fatty alkyl moiety of at least 16 carbons (including but not limited to palmitate amine or stearamine), polyacrylic acids, polysaccharide gums (including but not limited to Xanthan Gum), colloidal clays (including but not limited to benzyl dimethyl hydrogenated tallow ammonium montmorillonite), colloidal silica, triethanolamne, ethanol, cetyl alcohol, cetrimonium bromide, citric acid, cyclomethicone, dimethicone, ceteth 20, ceteareth 20, caprylic/capric triglycerides, PEG 40 polyhydroxystearate, polyvinyl pyrrolidone, acetum, glyceryl stearate, xanthan gum, geranium oil, lavender oil, eucalyptus oil, tea tree oil, lemon oil, anise oil, DEA cetyl phosphate, sodium stearate, potassium stearate, wool alcohols, octyl stearate, carnauba wax, ozokerite, carbomer, phenoxyethanol, methyl parabens and propyl parabens and mixtures thereof. While the amount of stabilizer used can be readily determined by those skilled in the art, suitable ranges include between about 1 to about 10% v/V.

In one of the preferred embodiments of the present invention the pediculicide composition is in the form of a conditioner or cream rinse for human hair or animal hair. Hair conditioning agents may be included in the formulation.

The pediculicide compositions of the present invention can be administered topically to an animal, by the direct laying on or spreading of the composition on the skin or hair, preferably of a mammal, most preferably of a human. The compositions useful in the subject invention involve formulations suitable for topical application to mammalian skin or hair. Additionally, the compositions may be made into a wide variety of product types. These include, but are not limited to solutions, aerosols, lotions, creams, gels, sticks, ointments, pastes, cream rinses, shampoos, and body washes. The preferred embodiments are cream rinses, conditioners and shampoos.

Vehicles include, but are not limited to, water, propylene glycol, butylene glycol, ethanol, isopropanol, silicones. Preferably, the vehicle is water.

In some embodiments, the pediculicide compositions of the present invention may further include other known pediculicides. Such agents are well known in the art and are present in many commercial pediculicide compositions, including (without limitation) nonoxynol, pyrethrins, piperonyl butoxide, permethrin, malathion, carbaryl, cuprex, phenothrin, DDT, neostigmine, prostigmine, lindane, phenothrin, propoxur, limonene, methoprene and cyromazine.

The methods of the present invention provide for topically contacting a composition as described above with a hair-bearing surface of a warm-blooded animal or surfaces that have been in contact with lice. For example, the surface may be infested with lice, infested with ova ("nits") or infested with a combination thereof. If the composition is applied to a surface that is infested with lice, the composition may be applied in order to immobilize and remove the lice. If the composition is applied to a surface that is infested with ova, the composition may be applied in order to inactivate and ease the subsequent removal of ova from the surface, whether dead, immobilized, or alive.

In some embodiments, the surface to which the composition is to be applied is a human body. Lice are found, on humans, most commonly, where hair is found on the body. Such areas include the scalp and hair on the scalp, the hairs of the genital region, the hair of the axilla, eyebrows, eyelashes, beards, and the body surface. In some embodiments, the surface is the head and hair on the head. In another embodiment, the surface is hair-bearing surface on the body of a human. In a further embodiment, the surface is the genital region of a human.

The treatment methods of the invention are achieved by topically applying a composition as described above. The composition may be topically applied to the surface by, for example, pouring the composition on the surface, or rubbing the composition over the surface. When the composition is topically applied as described above, the composition should thoroughly saturate the surface. In order to thoroughly saturate the surface with the composition, a sufficient or adequate amount of composition should be employed.

In a further embodiment, the methods of this invention comprise the further step of removing the immobilized lice from the treated surface, including for example, removal of immobilized lice or ova from the treated surface. This may be accomplished by combing the hair with a fine-toothed, lice removal comb after the composition has been topically applied, thereby lifting the lice or ova from the treated hair with the comb. In another embodiment, the surface may be washed or rinsed or washed and rinsed after the composition has been topically applied.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The following examples, which describe exemplary techniques and experimental results, are provided for the purpose of illustrating the invention, and should not be construed as limiting.

EXAMPLE 1

Pediculicide/Ovicide Composition

Two forms of pediculicide/ovicide composition were prepared:
Farnesol 1.0% w/w
Geranium oil 0.65% w/w
Lavender oil 0.65%/w
Eucalyptus oil 1.25% w/w
Olive oil (excipient) 2.4% w/w
Glyceryl monostearate (stabilizer) 8.0% w/w
Water (diluent) 84.46% w/w
Triethanolamine (pH adjuster) 0.34% w/w
Stearic acid (emulsifier) 1.30 w/w
and Farnesol 1.0% w/w
Olive oil (excipient) 2.4% w/w
Glyceryl monostearate (stabilizer) 8.0% w/w
Water (diluent) 85.98% w/w
Triethanolamine (pH adjuster) 0.34% w/w
Stearic acid (emulsifier) 1.3% w/w Farnesol, whilst found in many naturally occurring substances, may be isolated from sandalwood oil, obtained by solvent extraction and subsequent vacuum distillation from the heartwood of the tree *Santalum spicatum* occurring in Western Australia.

EXAMPLE 2

Treatment of Lice

Human lice, *Pediculus humanus*, were obtained from a culture colony and adult female and male lice, in approximately equal numbers, were used for each test.

The lice were fed on the morning of the test and allowed an appropriate period of time to recover, during which time they were able to excrete excess water imbibed with their blood meal. Lice were counted into batches that were provided with squares of close meshed nylon gauze, as a substrate upon which to stand, and each batch allocated to a marked 50 mm plastic Petri dish.

Louse eggs were obtained by providing egg laying adult lice with close meshed nylon gauze in pace of the normal corduroy substrate over a period of 24 hr. The lice were removed from the gauze, which was then cut into smaller pieces on which between 50 and 150 eggs were laid.

For the test procedure, approximately 2 mL of each of the pediculicide/ovicide compositions described in Example 1 were squeezed onto the gauze bearing the lice. It was spread carefully over the surface of the insects and the gauze to ensure even coverage. After application, the gauze and insects were returned to their marked Petri dish.

The same procedure was used to treat louse eggs.

However, in this case the application was repeated after 7 days (except for the groups treated overnight) to mimic the normal application regimen of the product.

The control test was performed using the same procedures but applying water spread over the lice or louse eggs in as near as possible the same way as the test product.

The treated lice were incubated under normal maintenance conditions (30° C.+2° C. and 50%+15% relative humidity) for the remainder of the test period. At the end of the test period, the lice and louse eggs were washed using a conditioner-free shampoo diluted into the ratio of one part shampoo to nine parts water. Observations of the lice to check for effect or recovery were made after washing and 1 hour later. No interim observations of the eggs were made.

The results of the test against lice were recorded approximately 18 hr after initial exposure. The results of the test against louse eggs were recorded after all eggs in the Control batches had completed hatching, approximately 11 days after the treatment.

In the tests described below, various exposure times were investigated to determine how long an exposure was required to kill lice or their eggs. The minimum time period was arbitrarily set at 40 minutes. This was based on the period of time required in a practical try out of the product in which a volunteer with moderately fine hair, cut to between the ears and shoulders, had some laboratory lice placed on the head, was treated, and combed through to remove the lice.

Lice in the Petri dish were immobile before washing and rinsing, mainly because the viscosity of the pediculicide/ovicide composition was such that lice could not move. After washing, the lice exhibited symptoms of intoxication. The physical signs were primarily those of spastic paralysis with the insect crossing their legs beneath the abdomen in a contorted manner. This was not entirely consistent with the signs that would be expected from an acetylcholine esterase inhibitor which would normally be present in the form of tonic clonic spasms and peripheral tremors. These signs were more reminiscent of those induced by pyrethroids and could constitute a mixture of effects from different components of the product.

The spasmic reaction was observed to continue for some time after the 1 hour assessment. However, by the time of the observation to record the results nearly all the insects had recovered normal gait. This recovery had also been sufficient that they had been able to lay a number of eggs, as shown in Table 1.

Identification of the activity of the composition on louse eggs was divided into a number of categories. Under most circumstances eggs that hatch are considered viable and unaffected by the treatment. These are listed as "Hatched" Table 2. Some eggs have embryos that develop fully but the young louse fails to emerge fully from the eggshell, either because residues of the product have an intoxicant effect on the louse or because the treatment renders the insect incompletely viable by dehydration or some other mechanism. These are listed as "Half-hatched" in results. Eggs in which the embryo develops to some extent but fails to open the cap of the eggshell are listed as "Dead". In some cases embryos may fail to develop, either because they are infertile or else because the product penetrates the eggshell and kills them at an early stage. These are listed as "Undeveloped" in reports of results.

TABLE 1

EFFECT OF PEDICULICIDE/OVICIDE COMPOSITION ON ADULT HUMAN LICE

| Treatment | Exposure time | Number of lice | | | | | Number of eggs |
|---|---|---|---|---|---|---|---|
| | | Total | Killed | Moribund | Alive | Mortality % | |
| Control | 40 min | 20 | 1 | 0 | 19 | 5 | 18 |
| Composition | 40 min | 20 | 1 | 0 | 19 | 5 | 14 |
| Control | 2 hours | 20 | 1 | 0 | 19 | 5 | 15 |
| Composition | 2 hours | 19 | 4 | 0 | 15 | 21 | 7 |
| Control | 4 hours | 20 | 0 | 0 | 20 | 0 | 14 |
| Composition | 4 hours | 21 | 13 | 0 | 8 | 62 | 6 |
| Control | Overnight | 21 | 0 | 0 | 21 | 0 | 18 |
| Composition | Overnight | 21 | 21 | 0 | 0 | 100 | 0 |

These results demonstrate a dose response relationship for the product, with longer exposure inducing a higher level of mortality. The 40 min exposure used on the basis that it was similar to the time required to comb through the hair to remove lice showed an effect on greater than the control group. However, increasing the exposure time beyond 2 hr demonstrated a pronounced effect on the lice. Those insects that did recover were able to lay some eggs, with diminishing numbers for longer exposure times.

An effect of the pediculicide/ovicide composition on louse eggs was detectable by comparison with the Control group.

By application of Abbot's correction to the results it was possible to adjust the figures to eliminate any effect due to natural mortality. Therefore, it was found that application for 40 min resulted in 8.2% of the eggs being inhibited from hatching, increasing to 28.1% following 2 hrs exposure, with complete inhibition after overnight exposure (Table 2).

TABLE 2

EFFECT OF PEDICULICIDE/OVICIDE COMPOSITIONS ON HUMAN LOUSE EGGS

| Treatment | Exposure time | Number of louse eggs | | | | Mortality % | Undeveloped % |
|---|---|---|---|---|---|---|---|
| | | Total | Hatched | Half-hatched | Dead | Undeveloped | |
| Control | 40 min | 130 | 121 | 0 | 7 | 2 | 6.9 | 1.5 |
| Composition | 40 min | 117 | 100 | 2 | 6 | 9 | 14.5 | 7.7 |
| Control | 2 hours | 113 | 100 | 1 | 8 | 4 | 11.5 | 3.5 |
| Composition | 2 hours | 160 | 97 | 0 | 30 | 33 | 39.4 | 20.6 |
| Control | Overnight | 138 | 109 | 4 | 11 | 14 | 21 | 10.2 |
| Composition | Overnight | 129 | 0 | 0 | 70 | 59 | 100 | 45.7 |
| Composition | Overnight | 100 | 0 | 0 | 44 | 56 | 100 | 56 |

Abott's correction is a mathematical formula that can be applied to experiments with living organisms that takes account of the mortality expressed by the Control group of organisms due to factors such as natural mortality and handling techniques.

The correction is applied by use of the formula:

$$M^1 = \frac{(M^t - M^c)}{(100 - M^c)} \times 100$$

Where:
$M^1$=Corrected mortality
$M^t$=Observed mortality in the Test group insects
$M^c$=Observed mortality in the Control group insects In normal use of the composition, a dose equivalent to a sufficient amount to thoroughly wet the hair and scalp of the user should be applied and allowed to stand for 40 min prior to combing out with a lice comb in the known manner. The hair should be washed in normal shampoo after treatment. Alternatively, the composition should be allowed to stand overnight before combing and washing.

Without being limited by theory, it is believed that the action of sesquiterpene alcohols and in particular, farnesol may mimic that of insect juvenile hormone. Those insects like lice which have the life cycle egg->larva->pupa->adult, produce juvenile hormones. Internal glands secrete hormones which control these stages. Juvenile hormone is one such, secreted by the corpora allata, two tiny glands in the head of an insect, juvenile hormone must be present for immature larva to progress through the usual stages of growth. Then, for mature larva to undergo metamorphosis into a mature adult, secretion must stop. If juvenile hormone is supplied at this time, the pupa does not form a viable, mature adult. Juvenile hormone must also be absent from insect eggs in order for them to undergo normal embryonic development. If the hormone is applied to the eggs, either they fail to hatch or the immature insects die without reproducing.

EXAMPLE 3

Treatment of Lice with Cream Formulation

A cream formulation comprising:

| | |
|---|---|
| Cetostearyl Alcohol | 7.5% |
| Cetrimide | 1.2% |
| Citric Acid | 1.0% |
| Dimethicone 350 | 5.0% |
| QN50 (farnesol) | 3.0% |
| Purified water | 82.3% | was prepared as an emulsion. This formulation was then independently tested against a control of 60% Isopropanol (IPA). This formulation was prepared in the manner described in Insect R&D Standard Operating Procedure No.: T.SOL.IPA.1 Edition No: 1.0.

The aim of this test was a dose response titration of one formulation against adult lice and their eggs. The selected times were 40 minutes 2 hours and overnight exposure time.

The test was performed using one replicate at each time point.

Human lice were obtained as described in Example 1. Adult female and male lice, in approximately equal numbers, were used for each test. The lice were fed on the morning of the test and allowed a minimum of 4 hours to recover, during which time they were able to excrete excess water imbibed with their blood meal. Lice were counted into batches that were provided with squares of fine meshed nylon gauze, as a substrate upon which to stand, and each batch allocated to a marked 50-millimeter plastic Petri dish.

Louse eggs were obtained by providing actively laying adult lice with a close meshed nylon substrate, in place of the normal cotton corduroy substrate, over a 48 hour period. At the end of this time the insects were removed and the gauze cut into appropriate sized smaller pieces. The small gauze pieces were randomly allocated to plastic Petri dishes in advance of the test.

Lice were then exposed as described in Example 1. Table 3 shows the efficacy of the formulation using exposure times of 40 minutes, 2 hours and overnight.

The figures indicate that at 40-minutes exposure the test formulation had little effect on lice i.e. 0% mortality, the same as the control group at this time point.

However, with 2-hours exposure the mortality rate rose to 73.7% with half the lice being killed and the remainder showing varying amounts of movement. With an overnight time point the test resulted in 100% mortality. In both cases the control group gave 0% mortality, showing the figures obtained as the true level of mortality.

Table 4 demonstrates the effect of the formulation on louse eggs with a 40-minute, 2 hours and an overnight exposure time.

The effect of the formulation against louse eggs at 40 minute resulted in only a small proportion dying before they could emerge. However with a 2 hour exposure the active material was able to kill nearly all the embryos before they commenced emergence. The low number of "Half hatched" eggs shows that in the majority of cases the lice did not reach the stage of starting to hatch but the low proportion (1.7%) of undeveloped eggs also shows that only a small quantity of active ingredient was able to penetrate the embryo, which could mean that using this treatment time in practice could allow the active ingredient to be washed away by subsequent hair washing before it had time to take effect.

The overnight application clearly demonstrated complete penetration of the embryo with none developing to the point where eyespots were visible, i.e., no later than 24 hours after treatment.

TABLE 3

EFFECT OF THE FORMULATION (WILD CHILD) AGAINST ADULT HUMAN LICE WITH A 40 MINUTE, 2 HOUR AND OVERNIGHT EXPOSURE - THICK GEL METHOD.

| | | | Number of lice | | | | Number of |
|---|---|---|---|---|---|---|---|
| Treatment | Replicate | Total | Killed | Moribund | Alive | Morality % | eggs |
| 40 minute | 1 | 20 | 0 | 0 | 20 | 0 | 0 |
| Control | 1 | 21 | 0 | 0 | 21 | 0 | 1 |
| 2 hour | 1 | 19 | 9 | 5 | 5 | 73.7 | 0 |
| Control | 1 | 20 | 0 | 0 | 20 | 0 | 0 |

TABLE 3-continued

EFFECT OF THE FORMULATION (WILD CHILD) AGAINST ADULT HUMAN LICE WITH A 40 MINUTE, 2 HOUR AND OVERNIGHT EXPOSURE - THICK GEL METHOD.

| Treatment | Replicate | Total | Number of lice | | | Morality % | Number of eggs |
|---|---|---|---|---|---|---|---|
| | | | Killed | Moribund | Alive | | |
| Overnight | 1 | 20 | 0 | 0 | 0 | 100 | 0 |
| Control | 1 | 20 | 0 | 0 | 20 | 0 | 2 |

TABLE 4

EFFECT OF THE FORMULATION (WILD CHILD QUIT NITS) AGAINST LOUSE EGGS WITH A 40 MINUTE 2 HOUR AND OVERNIGHT EXPOSURE TIME

| Treatment | Replicate | Total | Number of louse eggs | | | | Morality % | Undeveloped % |
|---|---|---|---|---|---|---|---|---|
| | | | Hatched | Half-hatched | Dead | Undeveloped | | |
| 40 minute | 1 | 277 | 168 | 2 | 98 | 9 | 39.4 | 3.2 |
| Control | 1 | 242 | 232 | 0 | 5 | 5 | 4.1 | 2.1 |
| 2 hour | 1 | 286 | 5 | 1 | 275 | 5 | 98.3 | 1.7 |
| Control | 1 | 250 | 241 | 0 | 5 | 4 | 3.6 | 1.6 |
| Overnight | 1 | 289 | 0 | 0 | 0 | 289 | 100 | 100 |
| Control | 1 | 283 | 255 | 2 | 18 | 8 | 9.9 | 2.8 |

The invention claimed is:

1. A pediculicide composition: consisting essentially of
(a) from about 1% w/w to about 5.0% w/w farnesol;
(b) from about 1% w/w to about 10% w/w of a stabilizer selected from the group consisting of glyceryl monostearate, stearic acid, triethanolamine, ethanol, polysorbate 20, cetyl alcohol, stearyl alcohol, cetrimonium bromide, citric acid, cyclomethicone, dimethicone, ceteth 20, ceteareth 20, caprylic/capric triglycerides, PEG 40 polyhydroxystearate, polyvinyl pyrrolidone, acetone, glyceryl stearate, xanthan gum, DEA cetyl phosphate, sodium stearate, potassium stearate, wool alcohols, octyl stearate, carnauba wax, ozokerite, carbomer, phenoxyethanol, methyl parabens, propyl parabens, and mixtures thereof;
(c) from about 0.5% w/w to about 5% w/w of oil selected from the group consisting of eucalyptus oil, olive oil, lemon oil, verbena oil, geranium oil, anise oil, patchouli oil, lavender oil, boronia oil, tea tree oil, bay oil, sandalwood oil, orange oil, citronella oil, grapefruit oil, jasmine oil, cinnamon oil, chamomile oil, clary sage oil, lime oil, mandarin oil, palma *rosa* oil, rosewood oil, ylang oil, hazelnut oil, nutmeg oil, and mixtures thereof;
(d) a synthetically derived excipient; and
(e) from about 80% w/w to about 95% w/w water, wherein the oil facilitates penetration of the farnesol into the chitin outer shell of a lice or a lice egg wall such that the lice or lice egg dies within a 24 hour exposure to the pediculicide composition.

2. The pediculicide composition according to claim 1, wherein the oil is olive oil.

3. The pediculicide composition according to claim 1, wherein the oil is selected from the group consisting of geranium oil, lavender oil, eucalyptus oil, olive oil, and mixtures thereof.

4. The pediculicide composition of claim 3 which consists of
(a) from about 1% w/w to about 5.0% w/w farnesol;
(b) from about 0.5% to about 5% w/w of olive oil as the oil;
(c) a synthetically derived excipient;
(d) from about 1% to about 10% w/w of glyceryl monostearate as the stabilizer;
(e) triethanolamine as a pH adjuster;
(f) stearic acid as a emulsifier; and
(g) from about 80% w/w to about 95% w/w water, wherein the oil facilitates penetration of the farnesol into the chitin outer shell of a lice or a lice egg wall such that the lice or lice egg dies within a 24 hour exposure to the pediculicide composition.

\* \* \* \* \*